United States Patent
Rauer et al.

(10) Patent No.: US 8,466,417 B2
(45) Date of Patent: Jun. 18, 2013

(54) RADIOMETRIC LEVEL OR DENSITY MEASUREMENT

(75) Inventors: Winfried Rauer, Fischerbach (DE); Josef Fehrenbach, Haslach (DE)

(73) Assignee: Vega Grieshaber KG, Wolfach (DE)

( * ) Notice: Subject to any disclaimer, the term of this patent is extended or adjusted under 35 U.S.C. 154(b) by 73 days.

(21) Appl. No.: 12/632,324

(22) Filed: Dec. 7, 2009

(65) Prior Publication Data

US 2010/0140480 A1 Jun. 10, 2010

Related U.S. Application Data

(60) Provisional application No. 61/120,537, filed on Dec. 8, 2008.

(30) Foreign Application Priority Data

Dec. 8, 2008 (EP) ..................... 08170957

(51) Int. Cl.
G01F 23/00 (2006.01)
(52) U.S. Cl.
USPC ..................................... 250/357.1
(58) Field of Classification Search
USPC ..................................... 250/357.1
See application file for complete search history.

(56) References Cited

U.S. PATENT DOCUMENTS 3,501,632 A * 3/1970 Kaminskas et al. ............ 378/52
6,879,425 B2 * 4/2005 Damm et al. ................. 359/272
7,778,787 B2 8/2010 Fiedler et al.

FOREIGN PATENT DOCUMENTS

| CN | 1473264 | 2/2004 |
|---|---|---|
| CN | 101006363 | 7/2007 |
| WO | 02/18883 | 3/2002 |
| WO | 2005/078397 | 8/2005 |

OTHER PUBLICATIONS

Nistor, "Moderne Radiometrische Fullstandmesstechnik" Messen Prufen Automatisieren, Hans Holzmann Verlag. Bad Worishofen, DE, No. 10, Oct. 1, 1998, pp. 496-500.
Eidsnes et al., "Scattered Gamma Radiation Utilized for Level Measurements in Gravitational Separators", 11(1)IEEE Sensors Journal, IEEE Service Center, New York, NY, vol. 5, No. 2, Apr. 1, 2005, pp. 175-182, XPO11128737, ISSN: 1530-437X.
Nistor, "Moderne Radiometrische Fullstandmesstechnik" Messen Prufen Automatisieren, Hans Holzmann Verlag. Bad Worishofen, DE, No. 10, Oct. 1, 1988, pp. 496-500.

* cited by examiner

Primary Examiner — Christine Sung
(74) Attorney, Agent, or Firm — Fay Kaplun & Marcin, LLP

(57) ABSTRACT

A level or density of a medium in a tank is radiometrically measured by detecting the light flashes generated by a scintillator with an array of photodiodes. Corresponding voltage pulses are summed up and analyzed with respect to their relevance before they are used for determining the level or the density of the medium.

10 Claims, 3 Drawing Sheets

US 8,466,417 B2

RADIOMETRIC LEVEL OR DENSITY MEASUREMENT

REFERENCE TO RELATED APPLICATIONS

This application claims the benefit of the filing date of EP Patent Application Serial No. 08 170 957.8 filed Dec. 8, 2008 and U.S. Provisional Patent Application Ser. No. 61/120,537 filed Dec. 8, 2008, the disclosure of which applications is hereby incorporated herein by reference.

FIELD OF THE INVENTION

The present invention relates to radiometric level or density measurements. In particular, the present invention relates to a radiometric level measurement system and/or a radiometric density measurement system for determining a level or a density of a medium, as well as to a method for radiometrically determining a level, namely for limit level measurements, or a density of a medium or for throughput measurements on conveyor belts or screw conveyors.

TECHNOLOGICAL BACKGROUND

In today's radiometric measurement systems, so-called photomultipliers are used that detect and convert the light flashes generated by a scintillator into an electric signal. Such photomultipliers may require a complicated voltage generation. Furthermore, the required space may be relatively large.

SUMMARY OF THE INVENTION

Disclosed is a radiometric level or density measurement system for determining a level or a density of a medium, as well as a method for radiometrically determining a level or a density of a medium.

The described embodiments equally apply to the measurement system and to the method. In other words, characteristics that are described below with reference to the measurement system may also be implemented in the method and vise versa.

According to one embodiment of the invention, a radiometric level measurement system and/or density measurement system for determining a level or a density of a medium in a tank is disclosed, wherein the measurement system features a converter, a photodiode and an evaluation unit. The converter serves for at least partially converting ionizing first radiation that penetrates the medium into electromagnetic second radiation. The photodiode serves for at least partially converting the second radiation into an electric signal, e.g. a voltage signal, and the evaluation unit serves for determining the level or the density of the medium based on a number of generated voltage pulses or voltage signals, respectively.

In other words, the electromagnetic signals (second radiation) being output by the converter are at least partially detected by the photodiode. The photodiode converts these electromagnetic signals into corresponding voltage signals that can then be counted. Prior to the counting, signals that correspond to one another (i.e., signals that are based on the same event) can be summed up.

Advantages of utilizing photodiodes may be seen in that they are small and that they can be inexpensively manufactured, as well as easily controlled. The combination of several photodiodes may make it possible to suppress blanking pulses of the photodiodes and to increase the sensitivity of the system.

An at least partial conversion of the ionizing radiation means that not the entire radiation that is emitted by the radioactive source and passes through the tank needs to be converted. It suffices if only a fraction of this radiation is converted. This applies analogously to the conversion of the radiation by the photodiode because the photodiode or the photodiode array also may not detect the entire radiation emitted by the converter, e.g., because part of this radiation passes the photodiodes.

According to another embodiment of the invention, the photodiode is an avalanche photodiode (APD).

A photodiode on the basis of a semiconductor is used rather than, for example, a photomultiplier that is based on tube technology. These photodiodes are smaller and easier to control than a photomultiplier. Avalanche photodiodes are advantageous because they have a very high sensitivity.

According to another embodiment of the invention, the converter is realized in the form of a scintillation counter or scintillator that converts the incident ionizing radiation into light flashes.

According to another embodiment of the invention, the measurement system furthermore features a comparator for converting the voltage pulse of the photodiode into a digital signal.

According to another embodiment of the invention, the evaluation unit is designed for counting the digital signals originating from the comparator or the voltage pulses.

According to another embodiment of the invention, the measurement system features a summation device for summing up digital signals that were created at the same time (i.e., signals that are based on the same event in the scintillator and therefore correspond to one another). The summation device then outputs a corresponding sum signal. In this case, the evaluation unit serves for counting only the sum signals with a predetermined minimum number of digital signals. The remaining sum signals are not counted, but rather discarded.

This may make it possible to prevent faulty measurements from negatively influencing the end result. In fact, only the signals are taken into account that were created at the same time and therefore caused by several light flashes that were generated in the scintillator by the same event such as, for example, by the same gamma quantum. Blanking pulses that are generated, e.g., due to the thermal inherent noise of the photodiode originate from different events and therefore do not occur simultaneously. These pulses thusly may be effectively suppressed.

According to another embodiment of the invention, the summation device is designed for summing up voltage pulses that were created at the same time and for outputting a corresponding sum signal, wherein the evaluation unit is designed for counting only the sum signals with a predetermined minimum pulse intensity. The remaining sum signals are once again discarded.

According to another embodiment of the invention, a method for radiometrically determining a level or a density of a medium is disclosed, wherein ionizing first radiation that penetrates the medium is at least partially converted into electromagnetic second radiation, e.g. light. This second radiation is at least partially converted into a voltage pulse with the aid of a photodiode. The level or the density of the medium is subsequently determined based on a detected number of generated voltage pulses.

Prior to the determination of the level or the density, the generated voltage pulses can be converted into digital signals that are subsequently counted.

It may be possible, in particular, to sum up the digital signals or the voltage pulses that were created at the same time in the above-described fashion. The corresponding sum signal is only used for the determination of the measured value if it fulfills a minimum requirement. A filter that only allows sufficiently strong signals to pass may be provided in order to decide whether or not the minimum requirement is fulfilled. If the digital signals are summed up, the minimum requirement consists of the sum signal having a certain minimum number of digital signals that were added to one another. If the voltage pulses are summed up, the minimum requirement consists of the resulting total pulse having a minimum pulse intensity or minimum amplitude, i.e., consisting of a sufficient number of individual pulses.

BRIEF DESCRIPTION OF THE FIGURES

Embodiments of the invention are described below with reference to the figures.

DETAILED DESCRIPTION OF EXEMPLARY EMBODIMENTS

The illustrations in the figures are schematic and not true-to-scale.

In the following description of the figures, the same reference symbols are used for identical or similar elements.

Figure 1:
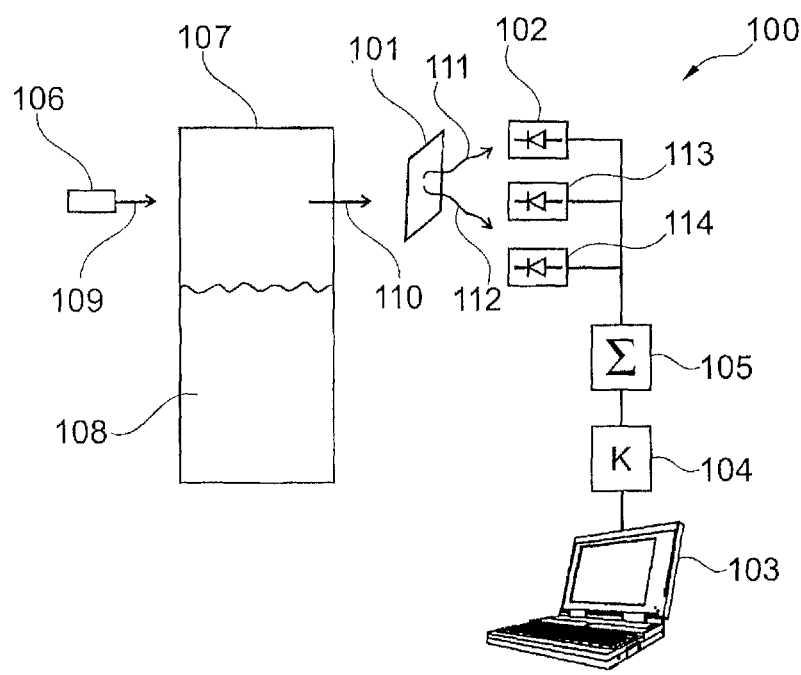
FIG. 1 shows an illustration of a measurement system according to one embodiment of the invention.

FIG. 1 shows an illustration of a measurement system according to one embodiment of the invention. The measurement system 100 features a radioactive source 106, a converter 101 in the form of a scintillation counter or scintillator, several photodiodes 102, 113, 114, a summation device 105, a comparator 104 and a microprocessor or evaluation unit 103. The evaluation unit 103 may be realized, for example, in the form of a computer.

The radioactive source comprises, for example, of a gamma radiator. The radioactive or ionizing radiation 109 generated by the source 106 is emitted in the direction of a container or tank 107. The container 107 contains a product 108, for example, in the form of a liquid, a solid or a gas. During the penetration of the container 107, the ionizing radiation 109 is attenuated to a degree that depends on the level or the density of the product 108. The (residual) radiation 110 emerging on the other side of the container is incident on the scintillation counter 101.

It should be noted that the radioactive source 106 may also comprise of an alpha radiator or a beta radiator.

The ionizing radiation or the ionizing particle incident on the scintillator 101 generates light flashes 111, 112. A gamma quantum can simultaneously generate hundreds to thousands of photons that are emitted at the same time and ultimately registered as an event. These light flashes (or the event) are recorded by the photodiodes 102, 113, 114 and converted into corresponding voltage pulses that correlate with one another.

The two voltage pulses that are created by the light flashes 111, 112 are summed up in the summation device 105 and converted into a digital signal in the comparator 104, wherein this digital signal is subsequently used for determining the level or the density of the medium by means of the evaluation unit 103 if the digital signal is caused by a minimum number of individual voltage pulses.

Figure 2:
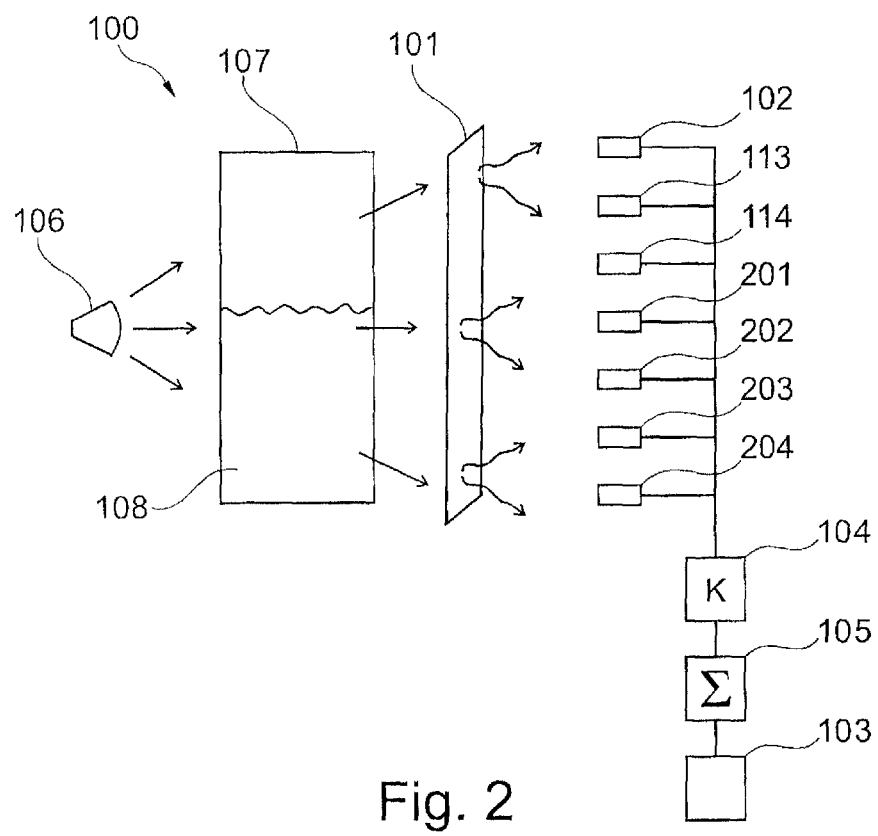
FIG. 2 shows an illustration of a measurement system according to another embodiment of the invention.

FIG. 2 shows another embodiment of such a measurement system 100, in which a radiation source 106 is used that emits radiation in several directions such that it penetrates a majority of the container 107 rather than a directional radioactive radiator 106 (according to FIG. 1).

The light flashes generated by the scintillator 101 are at least partially picked up by the diode array 102, 113, 114, 201 to 204 that may be realized two-dimensionally and converted into corresponding voltage pulses. All voltage pulses are subsequently digitized in the comparator 104. Corresponding digital signals are then summed up in the device 105 and forwarded to the evaluation unit 103 in the form of a sum signal.

Figure 3:
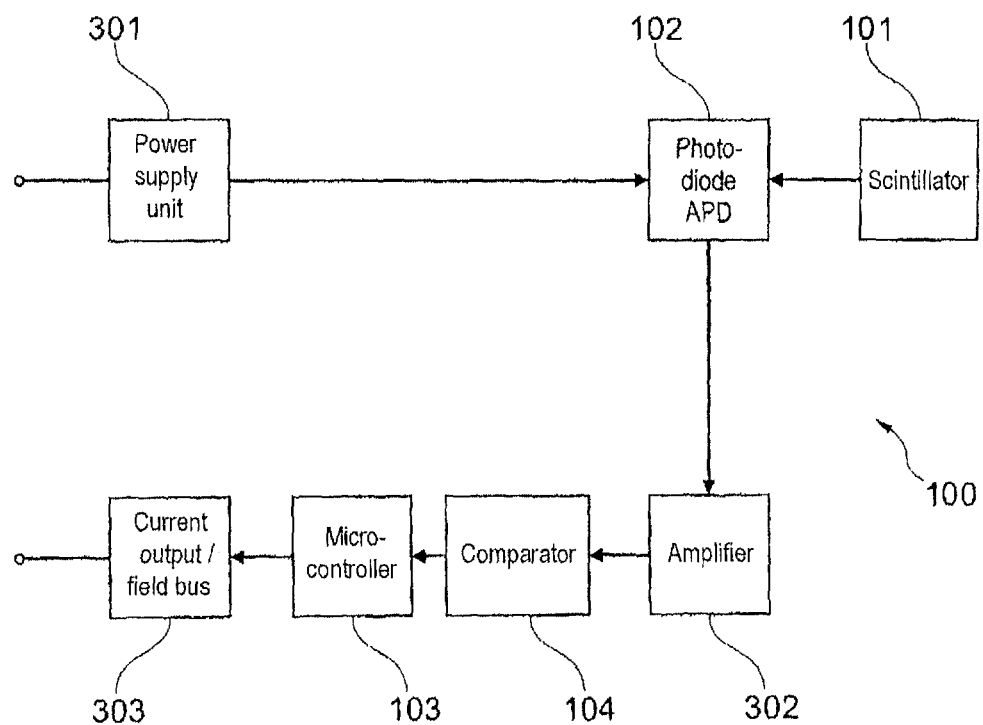
FIG. 3 shows an illustration of a measurement system according to another embodiment of the invention.

FIG. 3 shows a measurement system according to another embodiment of the invention. The measurement system comprises a power supply unit 301, a processor or microcontroller (evaluation unit) 103, a scintillator 101, one or more photodiodes 102, a signal amplifier 302, comparators 104 and a current output or field bus interface 303.

A voltage multiplication may also be provided.

The scintillator 101 converts radioactive gamma radiation of a radiation source into light flashes that, in turn, are converted into voltage pulses by the photodiode(s). The downstream signal amplifier amplifies these voltage, pulses. Comparators (for example, one for each diode) then convert the voltage pulses into digital pulses that are counted by the processor 103. The ionizing radiation is absorbed or attenuated in the container to a degree that depends on the process value (i.e., the level in the tank or the density conditions in the tank). This causes the pulse rate to change.

The processor 103 determines the physical process value from the pulse rate. Since semiconductor components are subject to inherent noise, unintentional pulses or so-called blanking pulses may occur, particularly with avalanche photodiodes. The active surface of the semiconductor diodes is smaller than that of photomultipliers.

The measuring result may be improved, however, if several photodiodes are used in a parallel fashion (as an array). This increases the size of the active surface and the inherent noise is simultaneously suppressed because the inherent noise of several diodes is not coherent. However, the measuring pulses are quite coherent if they are caused by the same ionizing event.

If the output pulses of the diodes are now summed up, coherent measuring pulses result in higher output pulses than non-coherent noise signals. This may make it possible to separate measuring signals that are based on an ionizing event from measuring signals that are based on noise.

It is also possible to initially convert the output pulses of the diodes into digital signals before the noise signals are separated from the measuring pulses by means of plausibility checks such as, e.g., a "two of three decision."

Figure 4:
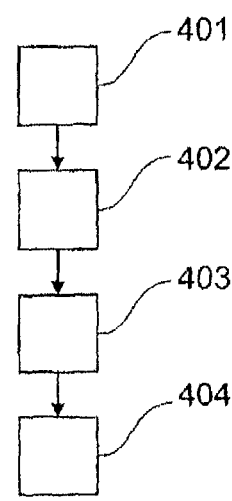
FIG. 4 shows a flow chart of a method according to one embodiment of the invention.

FIG. 4 shows a flow chart of a method, in which ionizing radiation is converted into electromagnetic radiation in step 401. In step 402, the electromagnetic radiation is subsequently converted into a voltage pulse with the aid of a photodiode. It is then evaluated whether the resulting signal is caused by an ionizing event or noise in step 403. In step 404, the signals that are identified as valid measuring signals are used for determining the level or the density of the medium.

Figure 5:
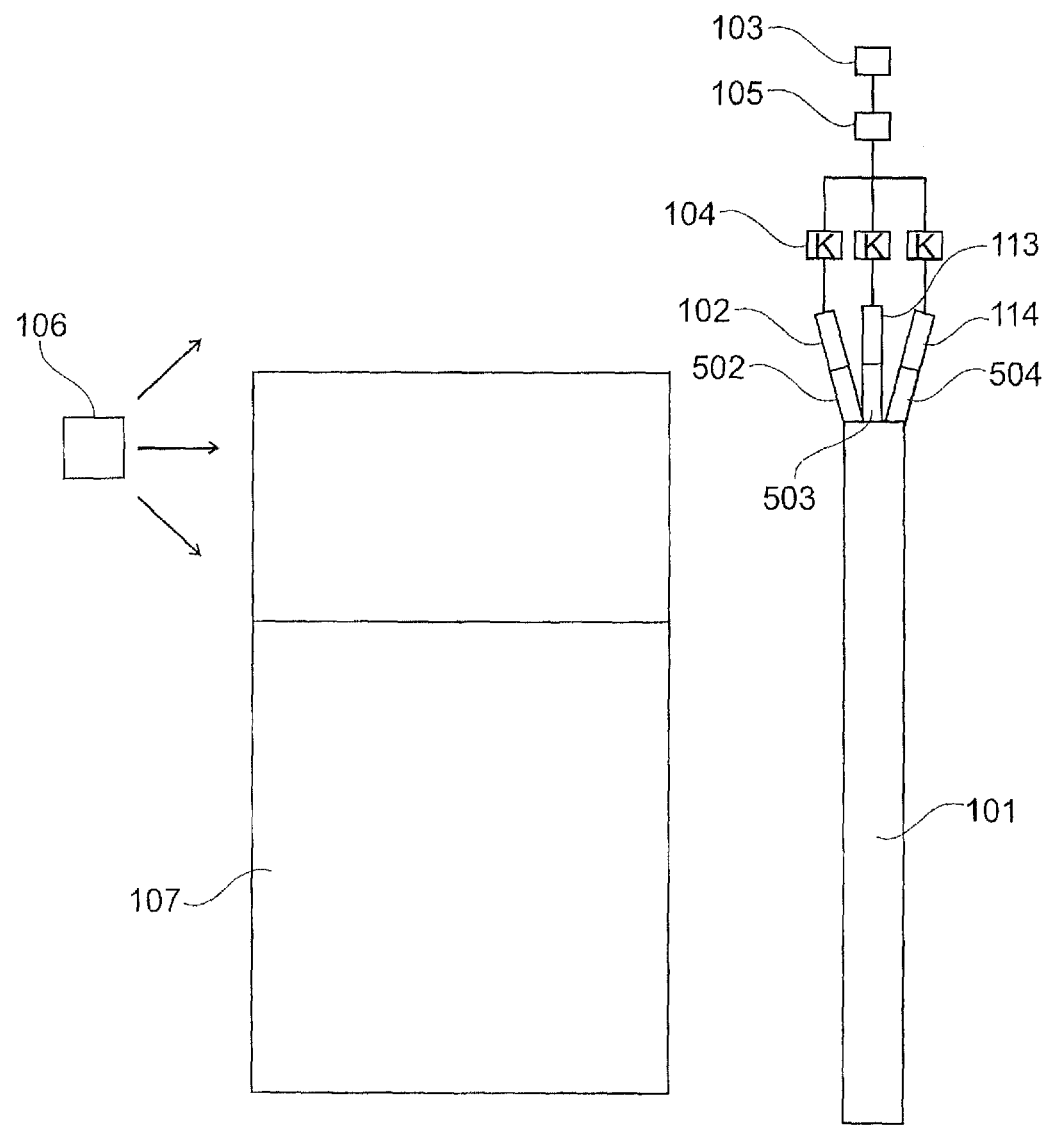
FIG. 5 shows an illustration of a measurement system according to another embodiment of the invention.

FIG. 5 shows a measurement system according to another embodiment of the invention, in which a radiation source 106 is used that emits radiation in several directions such that it penetrates a majority of the container 107 rather than a directional radioactive radiator (according to FIG. 1). Several photodiodes 102, 113, 114 are coupled to the scintillator 101 on the face (i.e., on the upper side and/or the underside). They may be connected to the scintillator by means of optical waveguides 502, 503, 504. The optical waveguides divide the light flashes being generated such that each photodiode receives and can detect part thereof.

Consequently, the light intensity being generated in the scintillator is measured rather than carrying out a vertically resolving measurement. The level or the density of the medium in the container can be determined based on the measured intensity that corresponds to the number of events (light flashes).

The optical waveguides may consist of plastic, glass or of scintillator material. Any other material that is able to guide the second electromagnetic radiation, e.g. light, is suitable for this purpose. Even a direct coupling of the photodiode to the scintillator or an air gap may be considered for this purpose.

One or more comparators 104 detect the signals of the photodiodes and generate voltage pulses. It is preferred to utilize at least one comparator per photodiode, A summation device 105 can sum up the voltage pulses of the comparators and forward the information to the evaluation unit 103 if a minimum number of comparators has simultaneously delivered a signal and the event consequently was caused by a measuring signal rather than a noise signal of the photodiode.

As a supplement, it should be noted that "comprising" and "featuring" do not exclude other elements or steps, and that "an" or "a" does not exclude a plurality. It should furthermore be noted that characteristics or steps that were described with reference to one of the above embodiments can also be used in combination with other characteristics or steps of other above-described embodiments. The reference symbols in the claims should not be interpreted in a restrictive sense.

The invention claimed is:

1. A measurement system for determining at least one of a level and a density of a medium, comprising:
    a converter at least partially converting ionizing first radiation that penetrates the medium into electromagnetic second radiation;
    a plurality of photodiodes at least partially converting the second radiation into a voltage pulse;
    an evaluation unit determining at least one of the level and the density based on a number of generated voltage pulses; and
    a summation device summing up digital signals that correspond to voltage pulses created at the same time and outputting a corresponding sum signal,
    wherein the evaluation unit is configured to utilize the sum signal only if it contains a predetermined minimum number of digital signals, and
    wherein the sum signal is treated as a noise signal and discarded if it does not contain a predetermined number of digital signals.

2. The measurement system of claim 1, wherein each of the plurality of photodiodes is an avalanche photodiode.

3. The measurement system of claim 1, wherein the plurality of photodiodes is arranged in a form of an array.

4. The measurement system of claim 1, wherein the converter is realized in the form of a scintillator.

5. The measurement system of claim 1, further comprising:
    a comparator converting the voltage pulse into a digital signal.

6. The measurement system of claim 5, wherein the evaluation unit counts the digital signals originating from one of the comparator and the voltage pulses.

7. A measurement system for determining at least one of a level and a density of a medium, comprising:
    a converter at least partially converting ionizing first radiation that penetrates the medium into electromagnetic second radiation;
    a plurality of photodiodes at least partially converting the second radiation into a voltage pulse;
    an evaluation unit determining at least one of the level and the density based on a number of generated voltage pulses; and
    a summation device summing up voltage pulses that were created at the same time and outputting a corresponding sum signal,
    wherein the evaluation unit is configured to utilize the sum signal only if it contains a predetermined minimum number of voltage pulses and wherein the sum signal is treated as a noise signal, if it does not have a predetermined minimum number of voltage pulses.

8. A method for radiometrically determining at least one of a level and a density of a medium, comprising:
    at least partially converting ionizing first radiation that penetrates the medium into electromagnetic second radiation;
    at least partially converting the second radiation into voltage pulses using a plurality of photodiodes;
    converting the voltage pulse into a digital signal;
    summing up digital signals that were created at the same time and outputting a corresponding sum signal, wherein only the sum signals with a predetermined minimum number of digital signals are counted;
    discarding the remaining sum signals as noise signals; and
    determining at least one of the level and the density based on the sum signals with the predetermined minimum number of digital signals.

9. The method of claim 8, further comprising:
    counting one of the digital signals and the voltage pulses.

10. A method for radiometrically determining at least one of a level and a density of a medium, comprising:
    at least partially converting ionizing first radiation that penetrates the medium into electromagnetic second radiation;
    at least partially converting the second radiation into voltage pulses using a plurality of photodiodes;
    summing up voltage pulses that were created at the same time and outputting a corresponding sum signal, wherein only the sum signals with a predetermined minimum number of voltage pulses are counted;
    discarding the remaining sum signals as noise signals; and
    determining the at least one of the level and the density based on the sum signals with the predetermined minimum pulse intensity.

* * * * *